(12) United States Patent
Hirayama et al.

(10) Patent No.: US 8,383,063 B2
(45) Date of Patent: Feb. 26, 2013

(54) MICROCHIP AND MICROCHIP MANUFACTURING METHOD

(75) Inventors: Hiroshi Hirayama, Musashino (JP); Toshinori Takimura, Hachioji (JP)

(73) Assignee: Konica Minolta Opto, Inc., Tokyo (JP)

( * ) Notice: Subject to any disclaimer, the term of this patent is extended or adjusted under 35 U.S.C. 154(b) by 191 days.

(21) Appl. No.: 13/059,370

(22) PCT Filed: Aug. 10, 2009

(86) PCT No.: PCT/JP2009/064119
§ 371 (c)(1),
(2), (4) Date: Feb. 16, 2011

(87) PCT Pub. No.: WO2010/021263
PCT Pub. Date: Feb. 25, 2010

(65) Prior Publication Data
US 2011/0142716 A1    Jun. 16, 2011

(30) Foreign Application Priority Data
Aug. 22, 2008  (JP) .................................. 2008-213572

(51) Int. Cl.
*G01N 15/06* (2006.01)
*G01N 33/00* (2006.01)
*G01N 33/48* (2006.01)

(52) U.S. Cl. ......... 422/503; 422/50; 422/68.1; 422/502; 264/1.1; 264/1.7; 156/60; 156/349; 156/381

(58) Field of Classification Search .................... 422/50, 422/502, 503; 264/1.1, 1.7; 156/60, 349, 156/381
See application file for complete search history.

(56) References Cited

U.S. PATENT DOCUMENTS
2004/0241049 A1  12/2004  Carvalho

FOREIGN PATENT DOCUMENTS
| JP | 64-018612 | 1/1989 |
| JP | 07-290902 | 11/1995 |
| JP | 2000-316013 | 11/2000 |
| JP | 2004-290968 | 10/2004 |
| JP | 2006-234600 | 9/2006 |

*Primary Examiner* — Brian J Sines
(74) *Attorney, Agent, or Firm* — Cozen O'Connor

(57) ABSTRACT

A microchip 1 in which a resinous film can be inhibited from sagging into a channel. The microchip 1 comprises: a resinous substrate 2 having a channel groove formed therein; and a resinous film bonded to a surface of the substrate on which the channel groove has been formed. A micro-channel 3 including channels 3A and channels 3B is formed by the channel groove and the resinous film 10. The total length of the channels 3B, which is parallel to the X direction for the resinous substrate 2, is larger than the total length of the channels 3A, which is parallel to the Y direction for the resinous substrate 2. The resinous substrate 2 has been bonded to the resinous film so that the sides parallel to the channels 3B are parallel to the TD direction of the resinous film and that the sides parallel to the channels 3A are parallel to the MD direction of the resinous film.

9 Claims, 4 Drawing Sheets

FIG. 8

| | EXAMPLE 1 | EXAMPLE 2 | COMPARISON EXAMPLE 1 | COMPARISON EXAMPLE 2 |
|---|---|---|---|---|
| BONDING CONDITIONS | 82 °C<br>38 kgf/cm²<br>30 SECOND | 82 °C<br>38 kgf/cm²<br>30 SECOND | 82 °C<br>38 kgf/cm²<br>30 SECOND | 82 °C<br>38 kgf/cm²<br>30 SECOND |
| ANNEALING CONDITIONS | 90 °C<br>60 MINUTES | 90 °C<br>60 MINUTES | 90 °C<br>60 MINUTES | 90 °C<br>60 MINUTES |
| TOTAL LENGTH OF CHANNEL 3B X | 60 mm | 100 mm | 60 mm | 100 mm |
| TOTAL LENGTH OF CHANNEL 3A Y | 40 mm | 20 mm | 40 mm | 20 mm |
| TOTAL X / TOTAL Y | 1.5 | 5 | 1.5 | 5 |
| FILM DIRECTION WITH RESPECT TO A SIDE PARALLEL TO CHANNEL 3B | TD DIRECTION | TD DIRECTION | MD DIRECTION | MD DIRECTION |
| FILM DIRECTION WITH RESPECT TO A SIDE PARALLEL TO CHANNEL 3A | MD DIRECTION | MD DIRECTION | TD DIRECTION | TD DIRECTION |
| AVERAGE DISTORTION AMOUNT OF CHANNEL 3B (BEFORE ANNEALING) | 1 μm | 1 μm | 2 μm | 2 μm |
| AVERAGE DISTORTION AMOUNT OF CHANNEL 3A (BEFORE ANNEALING) | 2 μm | 2 μm | 1 μm | 1 μm |
| AVERAGE DISTORTION AMOUNT OF CHANNEL 3B (AFTER ANNEALING) | 0.1 μm | 0.1 μm | 0.5 μm | 0.5 μm |
| AVERAGE DISTORTION AMOUNT OF CHANNEL 3A (AFTER ANNEALING) | 0.5 μm | 0.5 μm | 0.1 μm | 0.1 μm |
| DESIGN DEPTH OF CHANNEL | 30 μm | 30 μm | 30 μm | 30 μm |
| AVERAGE DEPTH ERROR OF CHANNEL 3B (BEFORE ANNEALING) | 3.3% | 3.3% | 6.7% | 6.7% |
| AVERAGE DEPTH ERROR OF CHANNEL 3A (BEFORE ANNEALING) | 6.7% | 6.7% | 3.3% | 3.3% |
| AVERAGE DEPTH ERROR OF ENTIRE CHANNEL (BEFORE ANNEALING) | 4.7% | 3.7% | 5.3% | 5.3% |
| AVERAGE DEPTH ERROR OF CHANNEL 3B (AFTER ANNEALING) | 0.33% | 0.33% | 1.67% | 1.67% |
| AVERAGE DEPTH ERROR OF CHANNEL 3A (AFTER ANNEALING) | 1.67% | 1.67% | 0.33% | 0.33% |
| AVERAGE DEPTH ERROR OF ENTIRE CHANNEL (AFTER ANNEALING) | 0.9% | 0.5% | 1.1% | 1.5% |
| DETECTION SENSITIVITY OF ANALYSIS OBJECT | B | A | C | C |
| REPRODUCIBILITY OF ANALYSIS OBJECT (VARIATION OF 10 REPEATS) | 5% | 3% | 7% | 15% |
| REPRODUCIBILITY OF ANALYSIS OBJECT | B | A | D | D |

SYMBOLS OF EVALUATION ITEMS
A: EXCELLENT, B: GOOD, C: FAIR, D: BAD

MICROCHIP AND MICROCHIP MANUFACTURING METHOD

RELATED APPLICATIONS

This application is a U.S. National Phase Application under 35 USC 371 of International Application PCT/JP2009/064119 filed Aug. 10, 2009.

This application claims the priority of Japanese application 2008-213572 filed Aug. 22, 2008, the entire content of which is hereby incorporated by reference.

TECHNICAL FIELD

The present invention relates to a microchip manufactured by bonding a resinous substrate on which a channel groove is formed and a microchip manufacturing method.

BACKGROUND

There are practically used devices so called a micro analysis chip, or a μTAS (Micro Total Analysis System) in which a micro-channel and a circuitry are formed on a silicon or a glass substrate via a micro technology so as to perform a chemical reaction, isolation and analysis of liquid specimens such as nucleic acid, protein and blood in a micro space. As a merit of the micro channel chip, it is considered that there is realized a space saving, portable and economical system which reduces amounts of sample and reagent used and an emission amount of waste liquid.

The microchip is manufactured by bonding two members wherein a microstructure is formed at least one member. Conventionally, a glass substrate is used for the microchip and various forming methods of forming the micro structure are suggested. However, since the glass substrate is not suitable for mass production and very costly, development of a low cost and disposable resinous microchip has been desired.

To manufacture the resinous microchip, a resinous substrate having a channel groove on a surface thereof and a resinous film to cover the channel groove are bonded. In the resinous substrate having the channel groove, through holes penetrating in a thickness direction of the resinous substrate are formed at ends of the channel groove and the like. The resinous substrate having the channel groove on the surface thereof is bonded with the resinous film for a cover with the channel groove inside. By the above bonding, the resinous film for the cover serves as a cover of the channel groove, thus a channel is formed with the channel groove and the resinous film. Whereby, the microchip having the channel inside is manufactured. Via the through holes formed on the resinous substrate, the channel and an outside of the microchip are connected, and liquid specimen enters and exits via the through holes.

As the method to bond the resinous substrate and the resinous film, there are cited a method to use an adhesive, a method to dissolve the resin surface for bonding, a method to use an ultrasonic welding, a method to use laser welding, and a method to use thermal fusion bonding via a pressure device having a role shape or a flat shape. Among the above methods, thermal fusion bonding is suitable as a bonding method, assuming mass production since it can be practiced at a low cost As the above microchip, there is suggested a microchip in which onto an acryl family resinous substrate such as polymethylacrylate, the same acryl family resinous film is bonded via thermal fusion bonding.

Prior Art Document

Patent Document
Patent Document 1: Unexamined Japanese Patent Application Publication No. 2000-310613

DISCLOSURE OF THE INVENTION

Problems to be Solved by the Invention

Based on a disclosure in the above Patent Document 1, the resinous substrate and the resinous film were bonded, however it was found that the resinous film sagged into the channel and the through hole. A cause of the resinous film bonded with sagging was revealed that the resinous film softened by heat is pushed into a space of the channel or the through hole by pressure.

In the state that the film is sagging into the channel groove, the channel formed by the channel groove and the resinous film becomes smaller that an original cross-section shape (rectangle or trapezium). Thus a flow speed of the liquid specimen flowing in the channel is reduced, and a variation of the flow speed occurs. As a result, an accurate measuring of the liquid specimen becomes difficult Also, the volume of the channel varies in accordance with the nature of sagging of the resinous film into the channel, an amount of the liquid specimen filling the channel varies. By the variation of the volume of the channel, a flowing direction and the flowing speed of the liquid specimen in the channel are effected. A large variation, namely a low quantitativeness, is a serious problem to carry out analysis of the liquid specimen. Also, by the variation of the volume of the channel, there is a problem that reproducibility is deteriorated.

Further by an increase of the sagging of the resinous film, the liquid specimen may leaks outside the microchip from a sagging portion of the resinous film in the channel. If the liquid specimen leaks out from the microchip, the quantitativeness of the liquid specimen is deteriorated and as a result, there is a problem such that analysis accuracy of the liquid specimen is deteriorated.

As above, in the microchip related to the prior art, by the sagging of the resinous film, the volume of the channel varies, and leakage of the liquid specimen occurs. As a result, there was a problem such that the analysis accuracy is deteriorated.

On aspect of the present invention is to resolve the above problem and an object of the present invention is to provide a microchip capable of inhibiting sagging of the resinous film and a manufacturing method of the microchip thereof

MEANS TO SOLVE THE PROBLEM

The present invention is focused on that the resinous film has different thermal contraction ratio in a MD direction and a TD direction of the resinous film. Here, the MD direction denotes a flowing direction of the film at manufacturing the film and the TD direction denotes a direction perpendicular to the MD direction.

A first embodiment of the present invention is a microchip in which a channel is formed having: a resinous substrate having a substantially rectangular outer shape in which a channel groove is formed, and a resinous film to form the channel by being bonded onto a surface of the resinous substrate on which the channel groove is formed, wherein a total length of a first channel parallel to a first side of the resinous substrate is longer than a total length of a second channel parallel to a second side, perpendicular to the first side, of the resinous substrate, of the resinous substrate, and the resinous substrate and the resinous film are bonded in a way that the first side and a TD direction of the resinous film are parallel and the second side and a MD direction of the resinous film are parallel.

Also a second embodiment of the present invention is a microchip in which a channel is formed having: a resinous substrate in which a channel groove is formed, and a resinous film to form the channel by being bonded onto a surface of the resinous substrate on which the channel groove is formed, wherein when the channel is disaggregated into a first channel representing an element parallel to a first side of a virtual rectangle surrounding the resinous substrate defined to be in contact with a periphery of the resinous substrate and a second channel representing an element parallel to a second channel perpendicular to the first side, a total length of the first channel is longer than a total length of the second channel, wherein the resinous substrate and the resinous film are bonded in a way that the first side and a TD direction of the resinous film are parallel and the second side and a MD direction of the resinous film are parallel.

Further, a third embodiment of the present invention is the microchip of the first or second embodiment, wherein the total length of the first channel is more than two times of the total length of the second channel.

Also, a fourth embodiment of the present invention is a manufacturing method of a microchip having a channel, having: bonding a resinous film via thermal fusion bonding onto a surface of a resinous substrate on which a channel groove is formed, wherein the resinous substrate in which the channel groove is formed, is in a substantially rectangular shape, wherein a total of a length of a first channel parallel to a first side of the resinous substrate is longer than a total of a length of a second channel parallel to a second side, perpendicular to the first side, of the resinous substrate, of the resinous substrate, and the resinous substrate and the resinous film are bonded in a way that the first side and a TD direction of the resinous film are parallel and the second side and a MD direction of the resinous film are parallel.

Also, a fifth embodiment of the present invention is a manufacturing method of a microchip having a channel, having: bonding a resinous film via thermal fusion bonding onto a surface of a resinous substrate on which a channel groove is formed, wherein the channel groove is formed in the resinous substrate, wherein when the channel is disaggregated into a first channel representing an element parallel to a first side of a virtual rectangle surrounding the resinous substrate defined to be in contact with a periphery of the resinous substrate and a second channel representing an element parallel to a second channel perpendicular to the first side, a total length of the first channel is longer than a total length of the second channel, wherein the resinous substrate and the resinous film are bonded in a way that the first side and a TD direction of the resinous film are parallel and the second side and a MD direction of the resinous film are parallel.

Also, a sixth embodiment of the present invention is the manufacturing method of the microchip of the forth or fifth embodiment, wherein the total length of the first channel is more than two times of the total length of the second channel.

Also, a seventh embodiment of the present invention is the manufacturing method of the microchip of any one of the forth to sixth embodiments, wherein a sagging amount of the resinous film in a cross-section in a width direction of the first channel is smaller that a sagging amount of the resinous film in a cross-section in a width direction of the second channel.

Also, an eight embodiment of the present invention is the manufacturing method of the microchip of any one of the forth to seventh embodiments wherein a sagging angle of the resinous film in a cross-section in a width direction of the first channel is smaller that a sagging angle of the resinous film in a cross-section in a width direction of the second channel.

Also, a ninth embodiment of the present invention is the manufacturing method of the microchip of any one of the forth to eighth embodiments, wherein the bonded resinous substrate and the resinous film is subject to annealing at a predetermined temperature.

EFFECT OF THE INVENTION

According to the present invention, the first side parallel to the first channel having a longer total length is made parallel to the TD direction of the resinous film, and the second side parallel to the second channel having a shorter total length is made parallel to the MD direction, whereby the width direction of the first channel and the MD direction having less sagging becomes parallel. Thus, since the sagging decreases in the width direction of the first channel having the longer total length, the sagging of the entire channel can be reduced.

DESCRIPTION OF THE DRAWINGS

FIG. 8 is a table showing conditions of examples and comparison examples.

DESCRIPTION OF THE PREFERRED EMBODIMENTS

Figure 1:
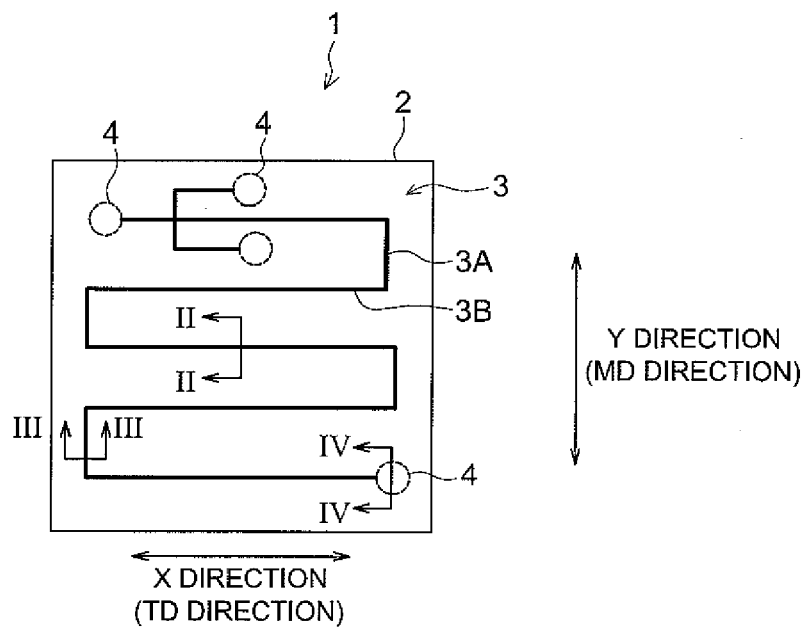
FIG. 1 is a top view of a microchip related to an embodiment of the present invention.
Figure 2:
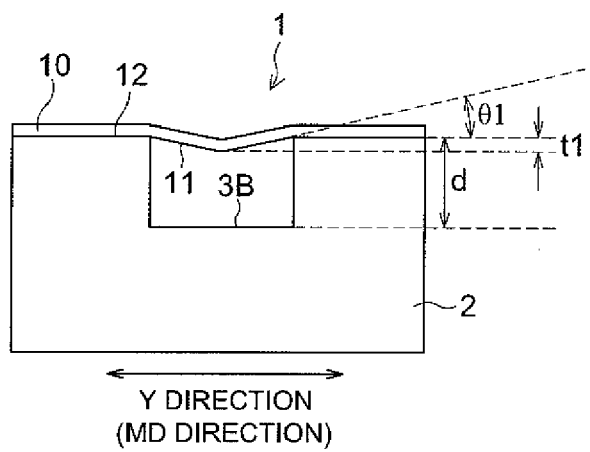
FIG. 2 is a cross-sectional view of a microchip related to an embodiment of the present invention and II-II section of FIG. 1.
Figure 3:
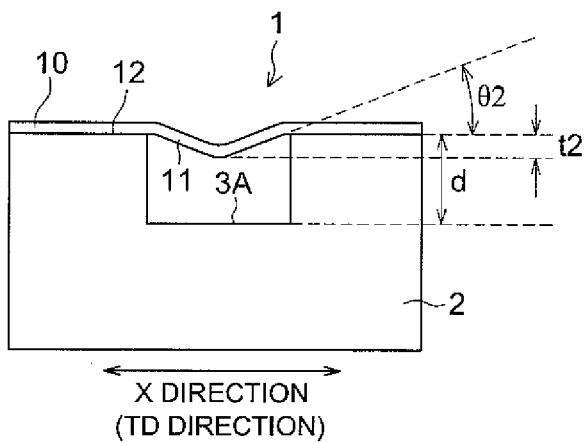
FIG. 3 is a cross-sectional view of a microchip related to an embodiment of the present invention and a II-III section of FIG. 1.
Figure 4:
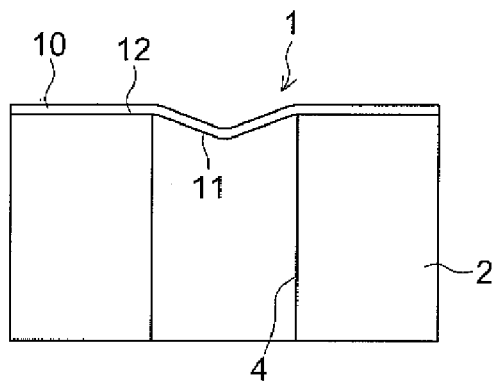
FIG. 4 is a cross-sectional view of a microchip related to an embodiment of the present invention and a IV-IV section of FIG. 1.

A microchip related to an embodiment of the present invention will be described with reference to FIG. 1 to FIG. 4. FIG. 1 is a top view of the microchip related to the present invention. FIG. 2 is a cross-section of a portion of the microchip related to the present invention and a II-II section of FIG. 1. FIG. 3 is a cross-section of a portion of the microchip related to the present invention and a III-III section of FIG. 1. FIG. 4 is a cross-section of a portion of the microchip related to the present invention and a IV-IV section of FIG. 1. FIG. 2 and FIG. 3 are cross-sectional views and FIG. 4 is a cross-sectional view of the through hole at a largest diameter.

As FIG. 1 to FIG. 3 show, the microchip 1 related to the present embodiment is provided with a resinous substrate 2 and a resinous film 10. On a surface of the resinous substrate 2 a channel groove is formed. The resinous film 10 representing a counterpart of bonding with the resinous substrate 2 is a member in a shape of a sheet. The resinous substrate 2 and the resinous film 10 are bonded with the surface on which the channel is formed (bonding surface) inside. Whereby, the resinous film 10 serves as a cover of the channel groove and a micro-channel 3 is formed, thus a microchip 1 having the micro channel 3 formed by the channel groove inside is manufactured. The micro channel 3 is configured with a bottom surface and walls of the channel groove, and a lower surface of the resinous film 10.

Also, as FIG. 1 and FIG. 4 show, in the resinous substrate 2, through holes 4 are formed to penetrate in a direction of the thickness of the substrate. The through holes 4 are formed at ends or in mid-course of the channel groove. By bonding the resinous substrate 2 and the resinous film 10 the through holes become opening sections which connect the micro channel with an outside. Since the through hole 4 is connected with the channel groove, the opening section of the through hole 4 is connected with the micro-channel 3. The opening section (through hole 4) is a hole to inlet, store and discharge gel, liquid regent or buffer liquid. A shape of the opening section (through hole 4) can be a cylindrical shape, a square shape or various shapes. A tube or a nozzle provided in the analyzer is connected to the opening (through hole 4) and gel, liquid regent or buffer liquid is inlet to the micro-channel 3 or discharged from the micro-channel 3.

A resin is used in the resinous substrate 2 and the resinous film 10. As resin conditions of the resin, there are cited a preferable formability (transferability and releasability), a high transparency, and a low self-fluorescence with respect to ultraviolet ray and visible ray. For example, a thermoplastic resin is used for the resinous substrate 2 and the resinous film 10. As the thermoplastic resin, for example, polycarbonate, polymethacrylate methyl, polystyrene, polyacrylnitryl, polyvinyl chloride, polyethylene terephthalate, nylon 6, nylon 66, polyvinyl acetate, polyvinylidene chloride, polypropylene polyisoprene, polyethylene, polydimethylsiloxane, cyclic polyolefin are cited. More preferably polymethacrylate methyl and cyclic polyolefin are used. Incidentally, the same material or different materials can be used for the resinous substrate 2 and the resinous film 10.

The resinous substrate 2 and the resinous film 10 are bonded via thermal fusion bonding. For example, using a heat plate, heat wind, a heat roller, ultrasonic, vibration or laser, the resinous substrate 2 and the resinous film 10 are heated and bonded. As an example, using a heat press machine, heated heat plates nip the resinous substrate 2 and resinous film 10, then pressure is applied and kept for a predetermined time, whereby the resinous substrate 2 and the resinous film 10 are bonded.

The size and shape of the resinous substrate 10 can be discretional as far as they facilitate handling and analysis, and a rectangular shape and a square shape are preferred. For example, 10 mm square to 200 mm square is preferable, and 10 mm square to 100 mm square is also preferable.

The shape of the micro-channel 3 is preferred to be in the range of 10 μm to 200 μm in the width and the depth without being limited thereto, in view of saving of the amount of the analysis specimen and the reagent to be used, as well as forming accuracy, transferring characteristics and mold releasability of the metal mold. Also, the width and the depth of the micro-channel 3 can be decided in accordance with use of the microchip. Incidentally, the shape of the cross-section of the micro-channel can be a rectangle or a curved shape.

The thickness of the resinous substrate 2 in which the micro-channel 3 is formed is preferred to be 0.2 mm to 5 mm in view of forming characteristic and 0.5 mm to 2 mm is more preferable. The thickness of the resinous film 10 (in a shape of a sheet) serving as the cover to encloses the channel groove is preferred to be 30 μm to 300 μm, and 50 μm to 150 μm is more preferable.

Here, the sagging of the resinous film 10 towards the channel groove when the resinous substrate 2 and the resinous film 10 are bonded will be described.
(Sagging Angle)

A sagging angle of the resinous film 10 will be described. In the cross-section in the width direction of the micro-channel 3, the sagging angle is defined as an angle θ which is formed with a tangent line at a discretional point on the lower surface 11 of the resinous film 10 forming a side of the micro-channel 3 and a bonding surface 12 between the resinous substrate 2 and the resinous film 10. If the wall of the channel groove of the resinous substrate 2 is perpendicular to the bonding surface 12, a possible range of the sagging angle θ is 0 to 90° (0°≦θ≦90°). Incidentally, the above sagging angle represents the sagging angle of the resinous film 10 in the cross-section in a width direction at each position of the channel. The sagging angle of the resinous film 10 in the cross-section in the width direction at each position of the channel is hereinafter may called " a sagging angle of the resinous film 10 in the channel".
(Sagging Amount)

Next a sagging amount t will be described. In a cross-section in the width direction of the micro-channel 3, a distance from a discretional point at the lower surface 11 of the resinous film 10 forming a side of the micro-channel 3 to the bonding surface 12 between the resinous substrate 2 and the resinous film 10 is defined as the sagging amount. The above distance is a length of a vertical line from the discretional point to a plane surface when the vertical line is drawn form the discretional point on the lower surface 11 of the resinous film 10 towards the plane surface which includes the bonding surface 12. Incidentally, the above sagging amount represents the sagging amount of the resinous film 10 in the cross-section in the width direction at each position of the channel. The sagging amount of the resinous film 10 in the cross-section in the width direction at each position of the channel is hereinafter may called as "sagging amount of the resinous film 10 in the channel".

In the above embodiment, as FIG. 1 shows, the resinous substrate 2 and the resinous film 10 have square outer shapes. Also, the micro-channel 3 is configured with a plurality of channels 3A parallel to a direction of a side (Y direction) of the microchip and a plurality of channels 3B parallel to a direction (X direction) perpendicular to the aforesaid side. Namely, a longitudinal direction of the channel 3A and the Y direction are parallel each other and a longitudinal direction of the channel 3B and the X direction are parallel each other. The channel 3A and the channel 3B are straight channels respectively and perpendicular to each other. As above, the micro-channel 3 is disaggregated into the channel 3A which is an element parallel to the Y direction and the channel 3B which is an element parallel to the X direction. At an end of the channel 3A, an end of the channel 3B perpendicular to the channel 3A is connected to form the micro-channel 3.

In the resinous film 10 having the square shape, one side is parallel to the MD direction (Machine Direction) and another side perpendicular the aforesaid side is parallel to the TD direction (Transverse Direction). The MD direction denotes a flow direction of the resin at manufacturing the resinous film 10, and the TD direction denotes a direction perpendicular to the MD direction.

The present embodiment focuses on the following two points to manufacture the microchip 1 by bonding the resinous substrate 2 and the resinous film 10.

(1) There is a difference in the thermal contraction ratio between the MD direction and the TD direction,
(2) In the microchip, the micro-channel is often designed to reciprocate so as to earn the length of the micro-channel. When this occurs, in the micro-channel, in order to increase the percentage of straight portions, a percentage of the straight portions parallel to a direction is increased.

Focusing the above tow points, the resinous substrate 2 and the resinous film 10 are bonded. Specifically, by comparing a total length X of the plurality of the channels 3B which longitudinal direction is parallel to the X direction and a total length Y of the plurality of the channels 3A which longitudinal direction is parallel to the Y direction, the TD direction of the resinous film 10 is set to coincide with the direction having the longer length, then the resinous substrate 2 and the resinous film 10 are bonded.

In the microchip 1 shown by FIG. 1, the plurality of the channels 3A and the plurality of the channels 3B are formed in the microchip 1 so that the total length X of the plurality of the channels 3B is longer than the total length Y of the plurality of the channels 3A. As above, in the embodiment shown in FIG. 1, the channels 3B represents the first channel which is parallel to the first side, and the channels 3A represents the second channel which is parallel to the second side. Since the longitudinal direction of the channels 3B is parallel to the X direction, the resinous substrate 2 and the resinous film 10 are bonded in a state that the X direction of the resinous substrate 2 and the TD direction of the resinous film 10 are parallel each other. Whereby, the X direction and the TD direction becomes parallel each other and the Y direction and the MD direction become parallel each other.

By bonding the resinous substrate 2 and the resinous substrate 10 in the above manner, as FIG. 2 shows, the width direction (Y direction) of the channel 3B coincides with the MD direction of the resinous film 10. Since the width direction of the channel 3B is perpendicular to the longitudinal direction of the channel 3B (X direction, TD direction), the width direction of the channel 3B becomes parallel to the MD direction of the resinous film 10. On the other hand, as FIG. 3 shows, the width direction (X direction) of the channel 3A coincides with the TD direction of the resinous film 10. Since the width direction of the channel 3A is perpendicular to the longitudinal direction (Y direction, MD direction) of the channel 3A, the width direction of the channel 3A becomes parallel to the TD direction of the resinous film 10.

The microchip 1 is manufactured by bonding the resinous substrate 2 and the resinous film 10 via thermal fusion bonding. As above, in case the resinous film 10 is heated, the resinous film 10 has a characteristic that the film tends to contract readily in the MD direction than in the TD direction. Thus when the resinous film 10 is bonded onto the resinous substrates 2 via thermal fusion bonding, the sagging amount the resinous film 10 in the MD direction is less than a sagging amount of the resinous film in the TD direction. Namely, in case the resinous substrate 2 and the resinous film 10 are bonded via thermal fusion bonding, the sagging amount of the resinous film 10 in the MD direction is relatively small, and the sagging amount of the resinous film 10 in the TD direction is relatively large. Also, the sagging angle of the resinous film 10 in the MD direction becomes smaller than the sagging angle in the TD direction. Namely, the sagging angle of the resinous film 10 in the MD direction becomes relatively small and the sagging angle of the resinous film 10 in the TD direction becomes relatively large.

In the present embodiment, the resinous substrate 2 and the resinous film 10 are bonded in a way that the longitudinal direction (X direction) of the channel 3B having the longer total length and the TD direction in which the sagging amount is large are made parallel, and the longitudinal direction (Y direction) of the channel 3A having the shorter total length and the MD direction in which the sagging amount is small are made parallel.

As above, by bonding the resinous substrate 2 and the resinous film 2 so that the MD direction in which the sagging amount of the resinous film 10 is small and the longitudinal direction (Y direction) of the channel 3A having the shorter total length are made parallel, as FIG. 2 shows, the width direction of the channel 3B having the longwe total length and MD direction having the small sagging amount are made parallel each other. Also the width direction of the channel 3B and the MD direction having the small sagging angle are made parallel. On the other hand by bonding the resinous substrate 2 and the resinous film 10 in a way that the TD direction having large sagging amount of the resinous film 10 and the longitudinal direction (X direction) of the channel 3B having the longer total length are made parallel, as FIG. 3 shows, the width direction of the channel 3A having the shorter total length and the TD direction having a large sagging amount become parallel. Also, the width direction of the channel 3A and the TD direction in which the sagging angle is large become parallel each other.

The sagging of the resinous film 10 in the channel 3A having the shorter total length has a small contribution to sagging of the entire micro channel 3 in accordance with the short length of the channel 3A. On the other hand, since the sagging amount of the resinous film 10 in the TD direction is relatively large, the sagging amount of the resinous film 10 in the TD direction has a large contribution to the sagging of the entire micro-channel 3. In the microchip 1 related to the present embodiment, by reducing a percentage of the TD direction with respect to the width direction of the micro-channel 3, the sagging amount of the entire micro-channel is reduced. For example, by making the TD direction having the large sagging amount of the resinous film 10 parallel to the width direction of the channel 3A having the short total length, the percentage of the TD direction with respect to the width direction of the micro-channel 3 can be reduced. As above since the percentage of the TD direction having the large sagging mount can be reduced, the sagging amount in the entire micro-channel 3 can be reduced. Also, by making the TD direction in which the sagging angle is large parallel to the width direction of the channel 3A having the longer total length, the sagging angle of the entire micro-channel 3 can be reduced.

Also, the sagging of the resinous film 10 in the channel 3B having the long total length has a large contribution to the sagging of the entire micro channel 3 in accordance with the longer length of the channel 3A. On the other hand, since the sagging amount of the resinous film in the MD direction is relatively small. Thus by making the MD direction having the small sagging amount of the resinous film 10 parallel to the width direction of the channel 3B having the longer total length, the sagging amount of the resinous film 10 in the channel 3B having a longer total length can be reduced. As above, since the sagging mount of the resinous film 10 in the channel 3B having the longwe total length can be reduced, the sagging amount in the entire micro-channel 3 can be reduced. Also, by making the MD direction in which the sagging angle is small parallel to the width direction of the channel 3B having the longer total length, the sagging angle of the entire micro-channel 3 can be reduced.

As above, by bonding the resinous substrate 2 and the resinous film 10 in the way that the width direction of the channel 3A having the shorter total length is made parallel to the TD direction of the resinous film 10, and the width direction of the channel 3B having the longer total length is made parallel to the MD direction of the resinous film 10, the sagging amount of the entire micro channel 3 can be reduced. Also, the sagging angle of the entire micro-channel 3 can be reduced. By reducing the sagging amount across the entire micro-channel 3, an error of the volume of the micro-channel can be reduced, thus analysis accuracy of the liquid specimen can be improved. Also, by reducing the sagging amount across the entire micro-channel 3, since the leakage of the liquid specimen from the microchip 1 can be inhibited, thus analysis accuracy of the liquid specimen can be improved.

Here the sagging angle θ and the sagging amount t of the resinous film 10 in the channel will be described with reference to FIG. 2 and FIG. 3

As FIG. 2 shows, in the channel 3B, the sagging angle is defined as a sagging angle θ1, and the sagging amount is defined as a sagging amount t1. On the other hand, as FIG. 3 shows, in the channel 3A, the sagging angle is defined as a sagging angle θ2, and the sagging amount is defined as a sagging amount t2.

In the present embodiment, the width direction of the channel 3B and the MD direction are parallel and the width direction of the channel 3A and the TD direction are parallel each other. Therefore, the sagging amount t1 in the channel 3B having the longer total length is smaller than the sagging amount t2 in the channel 3A having the shorter total length (t1<t2). Also, the sagging angle θ1 in the channel 3B is smaller than the sagging angle θ2 in the channel 3A (θ1<θ2).

As above, by bonding the resinous substrate 2 and the resinous film 10 in the way that the longitudinal direction of the channel 3B having the longer total length is made parallel to the TD direction, and the longitudinal direction of the channel 3A having the shorter total length is made parallel to the MD direction, the width direction of the channel 3B and the MD become parallel each other, and the width direction of the channel 3A and the TD direction become parallel each other. Thus the sagging amount of the resinous film 10 across the entire micro-channel 3 can be reduced. Also, the sagging angle across the entire micro-channel 3 can be reduced.

The total length X of the channel 3B having the longer total length is preferred to be more than two times of the total length Y of the channel 3A having the shorter total length. By making the total length more than two times, the percentage of the TD direction is reduced, thus the contribution to the sagging of the resinous film 10 in the TD direction is reduced. As the result, the sagging amount across the entire micro-channel 3 is reduced and the sagging angle can be reduced.

Incidentally, in case the micro-channel includes a curved channel, the total length can be obtained from the straight channel excluding the curved channel. Namely, excluding the curved channel, the total length X of the lengths of the channels parallel to the X direction and the total length Y of the lengths of the channels parallel to the Y direction have only to be compared.

Incidentally, the sagging angles θ1 and θ2 and the sagging amounts t1 and t2 are preferred to be the following values in view points of detection of the liquid reagent and flow of the liquid reagent. The sagging angles θ1 and θ2 are preferred to be 0° to 30°(0°≦θ1<30° and 0°≦θ2<30°) and 0 to 10° (0°≦θ1<10° and 0°≦θ2<10°) are more preferred. Also values of the sagging amounts t1 and t2 with respect to the depth d of the micro-channel 3 (channels 3A and 3B) are preferred to be 0 to 0.1 (0≦(t1/d <0.1 and 0<(t2/d)<0.1), and 0 to 0.05 (0≦(t1/d)<0.05 and 0≦(t2/d)<0.05) are more preferable.

(Measuring methods of sagging angle and sagging amount)

To measure the sagging angle and the sagging amount, a confocal scanning laser microscopy OLS 3000™ of Olympus Corporation was used. With a laser source of wave length λ=408 nm, a confocal optical system and a precision scanning mechanism, a highly accurate measuring is possible.

In case of measuring the sagging angle of the lower surface of the resinous film 10 forming a portion of the micro-channel 3, by radiating a laser light from an upper surface side of the resinous film 10, the lower surface 11 and the bonding surface 12 of the resinous film 10 were scanned by a laser focus and a three-dimensional shape of the lower surface 11 of the resinous film 10 was obtained. Then based on the three-dimensional shape, the sagging angle and the sagging amount of each position of the cross-section were obtained.

(Annealing Treatment)

After bonding the resinous substrate 2 and the resinous film 10 via thermal fusion bonding, the microchip 1 can be subject to annealing. It is considered that occurrence of sagging of the resinous film 10 at the micro-channel 3 and the through hole 4 means that by expansion of the resinous film 10 covering the channel groove and the through hole 4 or by applying pressure, the thickness of the resinous film 10 was reduced, as a result the area of the film was increased then the film was pushed into the channel groove and the through hole 4 in accordance with the increase of the area. Thus, by contracting the resinous film 10, the sagging of the resinous film 10 can be reduced. For example by heating the microchip 1 up to around a glass transition temperature, the resinous film 10 contracts and as a result, the sagging of the resinous film can be reduced. Since conditions of annealing such as heating temperature and heating time varies with physical characteristics of the resinous film 10, the thickness, the width of the channel groove and the diameter of the through hole 4, the conditions will be determined for each microchip. As an example, the sagging of the resinous film 10 can be reduced by annealing the microchip at 90° C. for one hour.

As a heating method, for example, a method to heat the microchip by leaving in a heated atmosphere using a constant-temperature reservoir to heat, a method to heat the surface of the microchip partially using a heat blower and a method to heat by radiating ultra violet ray onto the resinous film using a UV radiation device. Also, a longer heating time is effective to correct the sagging though there is a possibility of occurrence of deterioration of the resin, deformation of the micro-channel or deformation of the resinous substrate 2. Thus the annealing conditions are adjusted so as not to occur the deterioration and deformations.

MODIFICATION EXAMPLE 1

Figure 5:
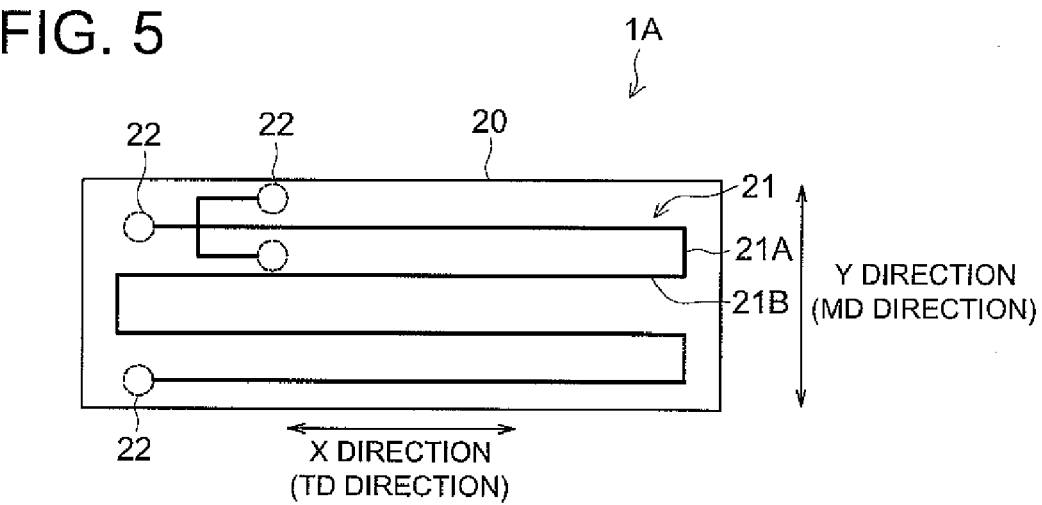
FIG. 5 is a top view of a microchip related to a modification example 1.

Next a modification example of the above embodiment will be described with reference to FIG. 5. FIG. 5 is a top view of the microchip related to the modification example 1.

A microchip 1A related to the modification example 1 is provided with a resinous substrate 20 having a channel groove formed on the surface thereof and a resinous film. By bonding the resinous substrate 20 and the resinous film with the surface on which the channel groove (bonding surface) is formed inside, a micro-channel 21 is formed with the channel groove by bonding the resinous substrate 20 and the resinous film, thus a microchip 1A having the micro-channel 21 by the channel groove inside is manufactured.

Also, in the resinous substrate 20, through holes 22 to penetrate the substrate in the thickness direction are formed. The through holes 22 are formed at ends of the channel groove or in mid-course of the channel groove. By bonding the resinous substrate 20 and the resinous film, the through hole serves as an opening section to connect the micro-channel 21 with an outside.

In the modification example 1, the resinous substrate 20 and the resinous film have rectangle outer shapes. A length (length in X direction) of one side of the microchip 1A is longer than a length (length in Y direction) of another side perpendicular to the aforesaid side. The micro-channel 21 is configured with a plurality of channels 21A parallel to a direction of the side (Y direction) of the microchip 1A and a plurality of channels 21B parallel to a direction (X direction) perpendicular to the side thereof. Namely, a longitudinal direction of the channel 21A is parallel to the Y direction and a longitudinal direction of the channel 21B is parallel to the X direction. The channel 21A and the channel 21B are straight channels and perpendicular to each other. As above, the micro-channel 21 can be disaggregated into the channel 21A representing an element parallel to the Y direction and the channel 21B representing an element parallel to the X direction. At an end of the channel 21A, an end of the channel 21B perpendicular to the channel 21A is connected so as to configure the micro-channel 21.

In the resinous film having the rectangular outer shape, one side is parallel to the MD direction and another side perpendicular to the aforesaid side is parallel TD direction.

In the same manner as the microchip 1 relate to the aforesaid embodiment, by comparing a total length X of the plurality of the channels 21B which longitudinal direction is parallel to the X direction and a total length Y of the plurality of the channels 21A which longitudinal direction is parallel to the Y direction, the TD direction of the resinous film 10 is made to coincide with the direction having a longer total length. Then the resinous substrate 20 and the resinous film are bonded.

In the microchip 1A related to the modification example 1, the plurality of the channels 21A and the plurality of the channels 21B are formed so that the total length X of the plurality of the channels 21B is longer than the total length Y of the plurality of the channels 21A. As above, in the modified example 1, the channel 21B represents the first channel which is parallel to the first side and the channel 21A represents the second channel which is parallel to the second side. Since the longitudinal direction of the channel 21B is parallel to the X direction, the resinous substrate 20 and the resinous film are bonded in a state that the X direction of the resinous substrate 20 and the TD direction of the resinous film are parallel each other. Whereby, the X direction and the TD direction become parallel each other and the Y direction and the MD direction become parallel each other.

As above by bonding the resinous substrate 20 and the resinous substrate, the width direction (Y direction) of the channel 21B and the MD direction of the resinous film coincide. On the other hand, the width direction (X direction) of the channel 21A coincides with the MD direction of the resinous film In the modification example 1, the resinous substrate 20 and the resinous film is bonded in a way that that the longitudinal direction (X direction) of the channel 21B having the longer total length and the TD direction in which the sagging amount is large are made parallel, and the longitudinal direction (Y direction) of the channel 21A having the shorter total length and the MD direction in which the sagging amount is small are made parallel.

As above, by bonding the resinous substrate 20 and the resinous film so that the width direction of the channel 21A having the shorter total length is made parallel to the TD direction of the resin film, and the width direction of the channel 21B having the longer total length is made parallel to the MD direction of the resin film, the sagging amount of entire micro-channel 21 is reduced and the sagging angle across the entire micro-channel 21 can be reduced in the same mariner as in the aforesaid embodiment.

MODIFICATION EXAMPLE 2

Figure 6:
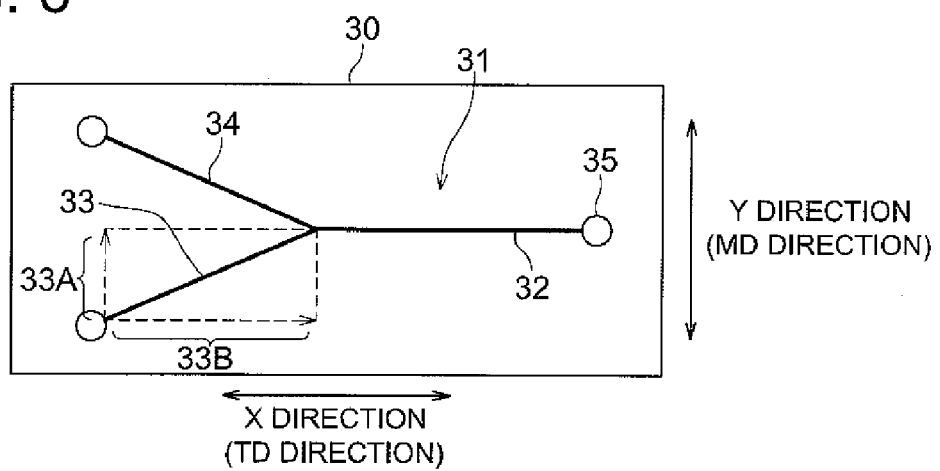
FIG. 6 is a top view of a resinous substrate related to a modification example 2.

Next, a modification example 2 of the above embodiment will be described with reference to the FIG. 6. FIG. 6 is a top view of the resinous substrate related to the modification example 2.

As FIG. 6 shows, the microchip related to the modification example 2 is provided with a resinous substrate 30 having a channel groove 31 formed on a surface thereof and a resinous film to be bonded onto the surface on which the channel groove 31 is formed. The micro-channel is formed by the channel groove 31, and a microchip having the micro-channel by the channel groove inside is manufactured. In the resinous substrate 30, through holes 35 penetrating the substrate in the thickness direction are formed.

In the modification example 2, the resinous substrate 30 and the resinous film have rectangular outer shapes. A length (length in the X direction) of one side of the resinous substrate 30 is longer than the length (length in the Y direction) of another side perpendicular to the aforesaid side. The channel groove 31 is, for example, in a Y character shape. Specifically, the channel groove 31 is configured with a channel groove 32 parallel to a direction of one side (X direction) of the resinous substrate 31 and channel grooves 33 and 34 extending obliquely from an end of the channel groove 32 with respect to the channel groove 32. As above, the channel grooves 33 and 34 are formed obliquely with respect to the side of the resinous substrate 30.

As above in the modification example 2, the channel grooves 33 and 34 are formed obliquely but not parallel to the X and Y directions of the resinous substrate 30. In the above case, the channel grooves 33 and 34 are disaggregated into an element of X direction and an element of Y direction parallel to respective sides of the resinous substrate 30. The channel groove 33 will be described as an example. As FIG. 6 shows, the channel groove 33 is disaggregated into a groove element 33A parallel to the Y direction and a groove element 33B parallel to the X direction. The channel groove 34 is also disaggregated into an element parallel to the X direction and an element parallel to the Y direction in the same mariner.

Then, a total length X of a length of the channel groove which longitudinal direction is parallel to the X direction and a length of the groove element parallel to the X direction is obtained. In the same manner, a total length Y of a length of the groove element which longitudinal direction is parallel to the Y direction and a length of the groove element parallel to the Y direction is obtained. Then comparing the total length X and the total length Y, the resinous substrate 30 and the resinous film are bonded so that the direction having the longer total length is coincided with the TD direction of the resinous film.

For example, by adding a length of the channel groove 32, a length of the groove element 33B, and a length of the element of the X direction of the channel groove 34, a total length X (a total of the first channel) is obtained. Also, by adding a length of the groove element 33A and a length of the element in the Y direction of the channel groove 34, a total length Y (a total of the second channel) is obtained. Then based on the total length X and the total length Y, a longer channel is judged. Namely, by comparing the total length X and the total length Y, the resinous substrate 30 and the resinous film are bonded so that the TD direction of the resinous film is coincided with a direction having longer total length (first side). In the modification example 2, since the total length X is longer than the total length Y, the resinous substrate 30 and the resinous film are bonded in a state that the X direction is a direction parallel to the first side, and the X direction of the resinous substrate 30 and the TD direction of the resinous film are parallel. Whereby, the X direction and the TD direction become parallel, and the Y direction and the MD direction become parallel.

By bonding the resinous substrate 30 and the resinous film in the above manner, the direction X having the longer total length including the length of the groove element and the TD direction in which the sagging amount is large are parallel, and the direction Y having the shorter total length including the length of the groove element and the MD direction in which the sagging amount is small are parallel. Namely, the width direction of the channel (Y direction) having the longer total length which includes the length of the groove element and the MD direction in which the sagging amount is small become parallel, and the width direction of the channel (X direction) having the shorter total length which includes the length of the groove element and the TD direction in which the sagging amount is large become parallel.

As above, by bonding the resinous substrate 30 and the resinous film so that the width direction of the channel having the shorter total length which includes the length of the groove element and the TD direction in which the sagging amount is large become parallel, and the width direction of the channel having the longer total length which includes the length of the groove element and the MD direction in which the sagging amount is small become parallel, the sagging amount across the entire micro-channel can be reduced in the same manner as the aforesaid embodiment.

MODIFICATION EXAMPLE 3

Figure 7:
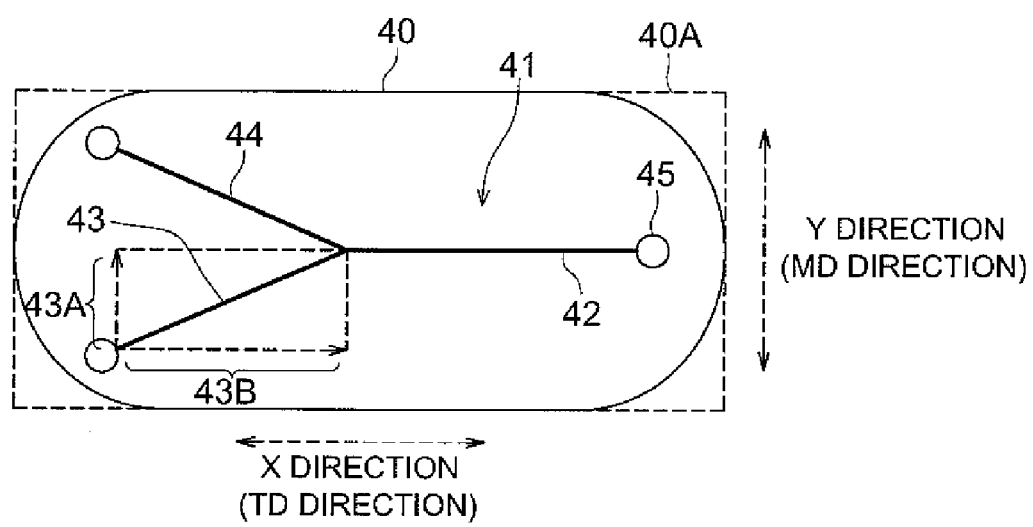
FIG. 7 is a top view of a resinous substrate related to a modification example 3.

Next, a modification example 3 of the above embodiment will be described with reference to FIG. 7. FIG. 7 is a top view of the resinous substrate related to the modification example 3.

As FIG. 7 shows, the microchip related to the modification example 3 is provided with a resinous substrate 40 having a channel groove 41 formed on a surface thereof and a resinous film to be bonded onto the surface on which the channel groove 41 is formed. The micro-channel is formed by the channel groove 41, and a microchip having the micro-channel by the channel groove inside is manufacture. In the resinous substrate 40, through holes 45 penetrating the substrate in the thickness direction are formed.

In the modification example 3, the resinous substrate 40 and the resinous film have a rectangular outer shape of which corners are curved. The channel groove 41 is, for example, in a Y character shape. Specifically, the channel groove 41 is configured with a channel groove 42 in a straight line shape and channel grooves 43 and 44 extending obliquely from an end of the channel groove 42 with respect to the channel groove 42.

As above, in the modification example 3, the outer shape of the resinous substrate 40 is not a rectangular shape but includes curved portions. In this case, there is supposed a smallest rectangle to surround the resinous substrate 40, which contacts with the outer shape of the resinous substrate 40 in a way that the contact portion of the rectangle is the maximum. For example, as FIG. 7 shows, there can be obtained a virtual rectangle 40A to surround the resinous substrate 40, which contacts with the outer shape of the resinous substrate 40. In the above case, the rectangle is obtained so that the contact portion of the rectangle 40A is the maximum. A length (length in the X direction) of one side of the virtual rectangle 40A is longer than a length (length in the Y direction) of another side perpendicular to the aforesaid side.

In case the virtual rectangle 40A is defined as above, a longitudinal direction of the channel groove 42 is parallel to a side (in the X direction) of the rectangle 40A. On the other hand, the channel grooves 43 and 44 are formed obliquely with respect to the side of the virtual rectangle 40A.

As above, the channel grooves 43 and 44 are not parallel to the X and Y directions of the virtual rectangle 40A and formed obliquely. In the above case, in the same manner as the modification example 2, the channel grooves 43 and 44 are disaggregated into an element of X direction and an element of Y direction. For example, as FIG. 7 shows, the channel groove 43 is disaggregated into a groove element 43A (representing the first channel) parallel to the Y direction and a groove element 43B (representing the second channel) parallel to the X direction. In the same manner, the channel groove 44 is also disaggregated into an element parallel to the X direction and an element parallel to the Y direction.

Then, a total length X (total length of the first channel) of a length of the channel groove which longitudinal direction is parallel to the X direction and a length of the groove element parallel to the X direction is obtained. In the same manner, a total Y (total length of the second channel) of a length of the channel groove which longitudinal direction is parallel to the Y direction and a length of the groove element parallel to the Y direction is obtained. Then comparing the total length X and the total length Y, the resinous substrate 40 and the resinous film are bonded so that the direction having the longer total length (first side) is coincided with the TD direction of the resinous film.

For example, by adding a length of the channel groove 42, a length of the groove element 43B, and a length of the element in the X direction of the channel groove 44, a total length X is obtained. Also, by adding a length of the groove element 43A and a length of the element in the Y direction of the channel groove 44, a total length Y is obtained. Then, in the same manner as the modification example 2, based on the total length X and the total length Y, which channel is longer is judged. Namely, by comparing the total length X and the total length Y, the resinous substrate 40 and the resinous film are bonded so that the TD direction of the resinous film is coincided with the direction having the longer total length. In the modification example 3, since the total length X is longer than the total length Y, the resinous substrate 40 and the resinous film are bonded in a state that the X direction is a direction parallel to the first side and the X direction of the virtual rectangle 40A and the TD direction of the resinous film are parallel. Whereby, the X direction and the TD direction become parallel, and the Y direction and the MD direction become parallel each other.

By bonding the resinous substrate 40 and the resinous film in the above manner, the direction X having the longer total length which includes the length of the groove element and the TD direction in which the sagging amount is large are parallel, and the direction Y having the shorter total length which includes the length of the groove element and the MD direction in which the sagging amount is small are parallel. Namely, the width direction of the channel (Y direction) having the longer total length which includes the length of the groove element and the MD direction in which the sagging amount is small become parallel, and the width direction of the channel (X direction) having the shorter total length which includes the length of the groove element and the TD direction in which the sagging amount is large become parallel.

As above, by bonding the resinous substrate 40 and the resinous film so that the width direction of the channel having the shorter total length which includes the length of the groove element and the TD direction in which the sagging amount is large become parallel, and the width direction of the channel having the longer total length which includes the length of the groove element and the MD direction in which the sagging amount is small become parallel, the sagging amount across the entire micro-channel can be reduced in the same manner as the aforesaid embodiment.

Incidentally, in the modification examples 1, 2 and 3, annealing can be applied to the microchip. Also, the total length of the channel having a longer total length is preferred to be more than two times of the total length of the channel having shorter total length. Also, in case the micro-channel includes curved channels, the total length is obtained from the straight channel omitting the curved area thereof.

EXAMPLES

Next, a specific example of the above embodiment will be described with reference to FIG. 8 which is a table showing conditions of examples and comparison examples.

Each example will be described as follow. Each of the examples is case that the microchip 1 is subject to annealing after the resinous substrate 2 and the resinous film 10 are bonded.

Example 1

(Bonding of the Resinous Substrate 2 and the Resinous Film 10, Anneal)

A resinous substrate of channel side was manufactured with a injection mold machine by forming a transparent resin material of methyl methacrylate (acrylic family resin) (Delpet 70NH of Asahi Kasei Corporation), in which a channel groove having a width of 30 μm and a depth of 30 μm and a plurality of through holes 4 having an inner diameter of 2 mm are formed on a plate shape member having an outer dimensions of width of 25 mm×width of 25 mm×thickness of 1 mm. Here, the depth 30 μm of the channel groove is defined as a design value of the channel. The above resinous substrate on the channel side represents an example of the resinous substrate 2 related to the aforesaid embodiment As a resinous film 10, the transparent resin material of methyl methacrylate (acrylic family resin) (Acryplane™ of Mitsubishi Rayon Co., Ltd. thickness: 75 μm) is cut into a width of 25 mm×a width of 25 mm.

By bonding the resinous substrate 2 and the resinous film 10, a microchip 1 is manufactured. A micro-channel 3 is formed by the channel groove and the resinous film 10.

The micro-channel 3 is configured with a channel 3B parallel to the X direction and the channel 3A parallel to the Y direction.

In the example 1, the total length Y of the channel 3B was 40 mm.

Also, the total length X of the channel 3B was 60 mm.

As above, the total length X of the channel 3B is longer than the total length Y of the channel 3A. Also, a ratio (X/Y) of the total length X of the channel 3B to the total length Y of the channel 3A is 1.5.

(Bonding)

The resin film 10 is laminated on a bonding surface 12 of the resinous substrate 2 on which the channel groove is formed. In the example 1,since the total length X of the channel 3B is longer than the total length B of the channel 3A, the resinous film 10 is laminated on the resinous substrate 2 so that the longitudinal direction (X direction) of the channel 3B and the TD direction of the resinous film 10 become parallel, and the longitudinal direction (Y direction) of the channel 3A and the MD direction of the resinous film 10 become parallel.

In the above state, using a thermal press machine, the resinous substrate 2 and the resinous film 10 were nipped with thermal plates heated at a pressing temperature of 82° C. and applied a pressure of 38 kgf/cm$^2$, then maintained for 30 sec to bond the resinous substrate 2 and the resinous film 10. Whereby, the microchip 1 was manufactured by the above bonding.

(Measuring)

After bonding, the sagging amount of the resinous film 10 was measured with a confocal scanning laser displacement meter LT 9000™ of Keyence Corporation. The sagging amount is calculated from displacements at a channel, the opening section (through hole 4) and adjacent plane thereof by focusing the laser on the outermost surface of the film with an outer shape measuring mode. The sagging amounts are measure at a plurality of points and an average value was obtained.

Also, using the confocal scanning laser displacement meter LT 9000™ of Keyence Corporation, the depths of the channels 3A and 3B were measured to obtain deviations from the design value of depth (30 μm). Laser light was focused on the lower surface of the film (channel upper surface) and a bottom surface of the channel while the surfaces thereof being scanned by the laser light, and the depth was calculated from displacements of the two surfaces. The depths were measured at a plurality of points and an average value was obtained.

(Anneal)

Next, the microchip 1 was annealed by keeping the microchip 1 in a constant-temperature reservoir at 90° C. for one hour. After annealing, the sagging amount of the resinous film 10 in the micro-channel was measured. Also, by measuring the depths of the channels 3A and 3B, the deviation from the design value of the depth (30 μm) was obtained.

(Evaluation)

(Electrophoresis Test Using Microchip)

First, a glutirous polymer liquid (poly dimethylacrylamide, pDMA) was filled from a well (opening section). Since the substrate formed by PMMA has a hydrophilic nature, capillary action can be used for filling. The polymer liquid was filled in each well so that liquid levels are equated. Next, fluorescent labeled DNA having a base pairs number of 100 bp to 1,000 bp was dripped into specimen filling well (opening section), then a direct current was applied to inlet and to separate. Using a cofocal laser microscope to energize and detect at a predetermined detection section, it was observed that plug (band) of the DNA was separated while forming a plug flow. The same electrophoresis was carried out ten times and by calculating variation of fluorescence intensity, reproducibility of detection of the analysis object (DNA) was obtained. The reproducibility indicates the variation of the fluorescence intensity. Namely a smaller value of reproducibility means a smaller variation of the fluorescence intensity. In the example 1, an excellent result of the reproducibility of 5% was shown. As above, in the example 1, the variation of the fluorescence intensity was able to be reduced.

Example 2

In an example 2, the ratio between the total length Y of the channel 3A and the total length Y of the channel 3B was changed.

Specifically, the total length Y of the channel 3A was 20 mm.

Also, the total length X of the channel 3B was 100 mm.

Whereby, the ration between the total length X of the channel 3B and the total length Y of the channel 3A (X/Y) was 5.

In the example 2, since the total length X of the channel 3B is longer than the total length Y of the channel 3A, the resinous substrate 2 and the resinous film 10 are laminated in a way that the longitudinal direction of the channel 3B (X direction) and the TD direction of the resinous film 10 are parallel each other, and the longitudinal direction of the channel 3A (Y direction) and the MD direction of the resinous film 10 are parallel each other. In the above state the resinous substrate 2 and the resinous film 10 were bonded each other in the same conditions as in the example 1 and the microchip 1 was annealed in the same conditions. Then in the same manner as the example 1, the sagging amount of the resinous film 10 in the micro-channel 3 and the depth of the micro-channel 3 were measured before and after the annealing.

Then, an average value of the sagging amounts before and after annealing and the deviations from designed depth value (3 μm) were obtained.

(Evaluation)

An electrophoresis test was carried out under the same conditions as the example 1. The same electrophoresis was carried out ten times and by calculating variation of fluorescence intensity of the detection section, reproducibility of detecting the analysis object was obtained. An excellent result of the reproducibility of 3% was shown. Further, compared to the example 1, higher detection sensitivity was confirmed. An experiment of the detection sensitivity was carried out with an index that how much a density of the DNA can be lowered while detection is possible.

Comparison Example

Next, comparison examples with respect to the above examples 1 and 2 will be described. In the comparison example, the direction of laminating the resinous film 10 is set in an opposite direction with respect to the examples 1 and 2.

Comparison Example 1

In the comparison example 1, in the same manner as example 1, the total length Y of the channel 3A was 40 mm and the total length X of the channel 3B was 60 mm. A ratio (X/Y) of the total length X of the channel 3B to the total length Y of the channel 3A is 1.5.

(Bonding)

In the comparison example 1, the total length X of the channel 3B is longer than the total length Y of the channel 3A. Therefore, in the comparison example 1, the resinous film 10 is laminated on the resinous substrate 2 so that the longitudinal direction (X direction) of the channel 3B and the MD direction of the resinous film 10 become parallel, and the longitudinal direction (Y direction) of the channel 3A and the TD direction of the resinous film 10 become parallel.

(Evaluation)

An electrophoresis test was carded out under the same conditions as the aforesaid examples. The same electrophoresis was carried out ten times and by calculating variation of fluorescence intensity, reproducibility of detecting the analysis object (DNA) was obtained. The reproducibility became 7%. As above, according to the comparison example 1, compared to the examples 1 and 2, the reproducibility was deteriorated. Namely, in the comparison example 1 the variation of the fluorescence intensity increased. The above reproducibility has a sufficient value to be used depending on usage of analysis, however, it cannot be applied for a field such as medical analysis where a high reproducibility is required. Also the detection sensitivity resulted in a low value.

Comparison Example 2

In the comparison example 2, in the same manner as example 2, the total length Y of the channel 3A was 20 mm and the total length X of the channel 3B was 100 mm. The ratio (X/Y) of the total length X of the channel 3B to the total length Y of the channel 3A was 5.

(Bonding)

In the comparison example 2, the total length X of the channel 3B is longer than the total length Y of the channel 3A. Therefore, in the comparison example 2, the resinous film 10 is laminated on the resinous substrate 2 so that the longitudinal direction (X direction) of the channel 3B and the MD direction of the resinous film 10 become parallel, and the longitudinal direction (Y direction) of the channel 3A and the TD direction of the resinous film 10 become parallel.

(Evaluation)

An electrophoresis test was carried out under the same conditions as the aforesaid example. The same electrophoresis was carried out ten limes and by calculating variation of fluorescence intensity at the detection section, reproducibility of detecting the analysis object (DNA) was obtained. The reproducibility became 15%. As above, according to the comparison example 2, compared to the examples 1 and 2, the reproducibility was deteriorated. The above, the reproducibility will occur a problem in practice that labeling of DNA having close molecular mass each other or separation of protein becomes difficult. Also, the detection sensitivity resulted in a low value.

As above, according to the examples of the present invention, compared to the comparison examples, the sagging amount was possible to be reduced. Also, the error of the depth of the micro-channel was possible to be lowered. Further as to the detection sensitivity and reproducibility of the analysis object, more preferable results were obtained than that of the comparison examples.

Incidentally, the materials and the dimensions indicated in the aforesaid examples are examples without the invention being limited to the materials and the dimensions thereof. For example, in case the resins cited in the aforesaid embodiment are used, the same results as the examples can be obtained. Also, as to the microchips related to the modification examples 1 and 2, the same results as the examples can be obtained.

Description of The Symbols

1 and 1A: microchip
2, 20, 30 and 40: resinous substrate.
3: micro-channel
3A, 3B, 21, 21A and 21B: channel
4, 22, 35 and 45: through hole
10: resinous film
11: lower surface
12: bonding surface
31, 32, 33, 34, 41, 42, 43 and 44: channel groove

What is claimed is:

1. A microchip in which a channel is formed comprising:
   a resinous substrate having a substantially rectangular outer shape in which a channel groove is formed, and
   a resinous film to form the channel by being bonded onto a surface of the resinous substrate on which the channel groove is formed,
   wherein a total length of a first channel parallel to a first side of the resinous substrate is longer than a total length of a second channel parallel to a second side, perpendicular to the first side, of the resinous substrate, and the resinous substrate and the resinous film are bonded in a way that the first side and a TD direction of the resinous film are parallel and the second side and a MD direction of the resinous film are parallel.

2. A microchip in which a channel is formed comprising:

a resinous substrate in which a channel groove is formed, and a resinous film to form the channel by being bonded onto a surface of the resinous substrate on which the channel groove is formed, wherein when the channel is disaggregated into a first channel representing an element parallel to a first side of a virtual rectangle surrounding the resinous substrate defined to be in contact with a periphery of the resinous substrate and a second channel representing an element parallel to a second channel perpendicular to the first side, a total length of the first channel is longer than a total length of the second channel, wherein the resinous substrate and the resinous film are bonded in a way that the first side and a TD direction of the resinous film are parallel and the second side and a MD direction of the resinous film are parallel.

3. The microchip of claim 1, wherein the total length of the first channel is more than two times of the total length of the second channel, 4. A manufacturing method of a microchip having a channel, comprising:

bonding a resinous film via thermal fusion bonding onto a surface of a resinous substrate on which a channel groove is formed, wherein the resinous substrate in which the channel groove is formed, is in a substantially rectangular shape, wherein a total of a length of a first channel parallel to a first side of the resinous substrate is longer than a total of a length of a second channel parallel to a second side, perpendicular to the first side, of the resinous substrate, and the resinous substrate and the resinous film are bonded in a way that the first side and a TD direction of the resinous film are parallel and the second side and a MD direction of the resinous film are parallel.

5. A manufacturing method of a microchip having a channel, comprising:

bonding a resinous film via thermal fusion bonding onto a surface of a resinous substrate on which a channel groove is formed, wherein the channel groove is formed in the resinous substrate, wherein when the channel is disaggregated into a first channel representing an element parallel to a first side of a virtual rectangle surrounding the resinous substrate defined to be in contact with a periphery of the resinous substrate and a second channel representing an element parallel to a second channel perpendicular to the first side, a total length of the first channel is longer than a total length of the second channel, wherein the resinous substrate and the resinous film are bonded in a way that the first side and a TD direction of the resinous film are parallel and the second side and a MD direction of the resinous film are parallel.

6. The manufacturing method of the microchip of claim 4, wherein the total length of the first channel is more than two times of the total length of the second channel.

7. The manufacturing method of the microchip of claim 4, wherein a sagging amount of the resinous film in a cross-section in a width direction of the first channel is smaller that a sagging amount of the resinous film in a cross-section in a width direction of the second channel.

8. The manufacturing method of the microchip of claim 4, wherein a sagging angle of the resinous film in a cross-section in a width direction of the first channel is smaller that a sagging angle of the resinous film in a cross-section in a width direction of the second channel.

9. The manufacturing method of the microchip of claim 4, wherein the bonded resinous substrate and the resinous film is subject to annealing at a predetermined temperature.

* * * * *